(12) United States Patent
Iwata et al.

(10) Patent No.: US 6,774,269 B2
(45) Date of Patent: Aug. 10, 2004

(54) PROCESS FOR PRODUCING ISOPULEGOL

(75) Inventors: Takeshi Iwata, Hiratsuka (JP); Yoshiki Okeda, Hiratsuka (JP); Yoji Hori, Hiratsuka (JP)

(73) Assignee: Takasago International Corporation, Tokyo (JP)

( * ) Notice: Subject to any disclaimer, the term of this patent is extended or adjusted under 35 U.S.C. 154(b) by 389 days.

(21) Appl. No.: 10/045,157

(22) Filed: Jan. 15, 2002

(65) Prior Publication Data

US 2002/0133046 A1 Sep. 19, 2002

(30) Foreign Application Priority Data

Jan. 18, 2001 (JP) .................................... P. 2001-010527

(51) Int. Cl.[7] .............................................. C07C 35/08
(52) U.S. Cl. ........................ 568/828; 568/822; 568/832
(58) Field of Search ................................ 568/822, 828, 568/832

(56) References Cited

U.S. PATENT DOCUMENTS

| | | | |
|---|---|---|---|
| 6,177,596 B1 | 1/2001 | Yadav et al. | ................ 568/829 |
| 6,329,480 B1 | 12/2001 | Uchiumi et al. | ............ 526/173 |

FOREIGN PATENT DOCUMENTS

| | | |
|---|---|---|
| EP | 945 470 | 9/1999 |
| JP | 53116348 | 10/1978 |
| WO | WO 99/32422 | 7/1999 |

OTHER PUBLICATIONS

Nakatani, et al., "A Highly Stereoselective Preparation of *I*–Isopulegol", Synthesis (1978), pp. 147–148.
"Alkylaluminum Chloride Induced Cyclization of Unsaturated . . . ", J. Am. Chem. Soc. (1980), vol. 102, pp. 7951–7953.
Sakane, et al., "Asymmetric Cyclization of Unsaturated Aldehydes . . . ", Tetrahedron Letters, vol. 26, No. 45 (1985), pp. 5535–5538.
Funakoshi, et al., "Insight into the Cyclization of 6–Octen–1–als with . . . ", Chem. Pharm. Bull. vol. 37, No. 8 (1989), pp. 1990–1994.
Kropp, et al., "Surface–Mediated Reactions. 6. Effects of Silica Gel and . . . ", J. Org. Chem., vol. 6 (1995), pp. 4146–4152.
Marty, et al., "Diasteroselective Synthesis of (1S,2S,3R, 6S) 3–Chloro–3–methyl–6–isopropenyl–1,2–cyclohexandiol . . . ", Tetrahedron, vol. 52, No. 13 (1996), pp. 4645–4658.
Sarkar, et al., "Diiodosamarium, a Unique Catalyst Precursor for . . . ", Tetrahedron Letters, vol. 37, No. 29 (1996), pp. 5195–5198.
Aggarwal, et al., "Scandium Trifluoromethanesulfonate, an Efficient Catalyst . . .", Tetrah dron Letters, vol. 39 (1998), pp. 1997–2000.
Ellis, et al., "Homogeneous catalyst. Use of ruthenium(II) complex", Chem. Commun., (1998), pp. 1311–1312.
Yadav, et al., "Novelties of eclectically engineered sulfated . . . ", Chem. Commun. (1998), pp. 2369–2370.
Maruoka, et al., "Virtually Complete Blocking of $\alpha$–$\beta$–Unsaturated . . . ", J. Am. Chem. Soc., V I. 116 (1994), pp. 4131–4132.
Saito, et al., "Molecular Recognition of Carbonyl Compounds . . . ", J. Am. Chem. Soc., vol. 122 (2000), pp. 7847–7848.
Sakane, et al., Chem. Abs. Database Accession No. 104:109961 CA XP002260665 (Abstract).
Takasago Perfumery Co. (1978), Database No. XP 002260666 (Abstract).

*Primary Examiner*—Elvis O. Price
(74) *Attorney, Agent, or Firm*—Fitzpatrick, Cella, Harper & Scinto

(57) ABSTRACT

A process for producing l-isopulegol by simple operations with safety in high yield. A process for producing isopulegol, which comprises selectively cyclizing citronellal in the presence of a tris(2,6-diarylphenoxy)aluminum catalyst represented by the following general formula (3):

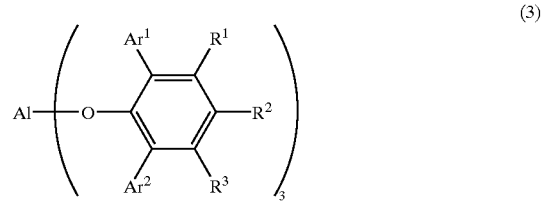

(3)

wherein Al represents an aluminum atom, $Ar^1$ and $Ar^2$ each represent a substituted or unsubstituted aryl group or a heteroaryl group; and $R^1$, $R^2$ and $R^3$ each represent a hydrogen atom, a halogen atom, an alkyl group having 1 to 8 carbon atom(s), an alkoxy group having 1 to 8 carbon atom(s), a substituted or unsubstituted aryl group, a dialkylamino group having 1 to 4 carbon atom(s), or a nitro group.

3 Claims, No Drawings

PROCESS FOR PRODUCING ISOPULEGOL

FIELD OF THE INVENTION

This invention relates to a process for producing isopulegol which is a useful material for making aromas and an important precursor for synthesizing menthol.

BACKGROUND OF THE INVENTION

Menthol, particularly l-menthol is extraordinary important as an aroma with coolness and has been finding wide applications in a variety of fields. Known methods of synthesizing menthol are divided into optical resolution of dl-menthol and asymmetric synthesis (see Indoh Moto-ichi, Gosei Koryo, Kagaku Kogyo Nipposha, pp. 106–114). In the route of asymmetric synthesis, l-menthol is obtained by hydrogenation of l-isopulegol as a precursor. Synthesis of the l-isopulegol involves selective cyclization of d-citronellal as an important step.

The process of producing l-isopulegol comprising selectively cyclizing d-citronellal in the presence of zinc bromide as a catalyst, which is disclosed in JP-A-53-116348 and Nakatani and Kawashima, *Synthesis*, p. 147 (1978), has already been put to practical use. In this process, the ratio of l-isopulegol to other isomers is 94/6.

Other catalysts hitherto reported for selective cyclization of citronellal include $Me_2AlCl$ (Micheal, K. and Snider, B. B., *J. Am. Soc.*, 102, pp. 7951–7953 (1980)), Zn(binaphthol) (Sakane, S. et al., *Tetrahedron Lett.*, vol. 26, No. 45, pp. 5535–5538 (1985)), $RhCl(PPh)_3$ (Funakoshi, K. et al., *Chem. Pham. Bull.*, vol. 37, No. 8, pp. 1990–1994 (1989)), an acid catalyst supported on a silica gel or alumina carrier (Kropp, P. J., *J. Org. Chem.*, vol. 60, pp. 4146–4152 (1995)), Zn/trimethylsilyl chloride (Marty, M. et al., *Tetrahedron*, vol. 52, No. 13, pp. 4645–4658 (1996)), $SmI_2$ (Sarkar, T. K. and Nandy, S.K., *Tetrahedron Lett.*, vol. 37, No. 29, pp. 5195–5198 (1996)), Sc(trifluoromethane sulfonate)$_3$ (Aggarwal, V.K. et al., *Tetrahedron Lett.*, vol. 39, pp. 1997–2000 (1998) and International Publication WO 99/32422), trans-[Ru(salen) (NO) $(H_2O)]^+$ (Ellis, W. W. et al., *Chem. Commun.*, pp. 1311–1312 (1998)), $S-ZrO_2$ (Yadav, G.D. and Nair, J.J., *Chem. Commun.*, pp. 2369–2370 (1998)), and solid catalysts (JP-A-11-267524). None of these catalysts is superior in selectivity to isopulegol to zinc bromide that have been used in industry.

Sc(trifluoromethane sulfonate)$_3$ is equal to zinc bromide in selectivity only when the reaction is conducted in an extremely low temperature of −78° C. The selectivity to l-isopulegol reduces to 80% at room temperature, which is insufficient for industrialization.

The catalyst of the present invention, a tris(2,6-diarylphenoxy)aluminum, is reported as a catalyst for polymerization (JP-A-11-335432) or aldol condensation (Yamamoto, H. et al., *J. Am. Chem. Soc.*, vol. 116, pp. 4131–4132 (1994), Yamamoto, H. et al., *J. Am. Chem. Soc.*, vol. 122, pp. 7847–7848 (2000)). Application of this catalyst to cyclization reactions, still less to synthesis of isopulegol, has not been reported nor known.

SUMMARY OF THE INVENTION

An object of the present invention is to provide a process for obtaining isopulegol through high-selectivity cyclization of citronellal, particularly a process for producing l-isopulegol, which is an important synthesis precursor for l-menthol and is useful as a material of perfumes, etc., by simple operations with safety in high yield.

As a result of extensive investigations, the present inventors have found that a specific catalyst enables citronellal to be cyclized to provide isopulegol in high yield and at such a selectivity as high as 98% or more based on the total isomers produced, i.e., isopulegol, isoisopulegol, neoisopulegol, and neoisoisopulegol. The present invention has been completed based on this finding.

The present invention includes the following embodiments.

1) A process for producing isopulegol represented by the following formula (1):

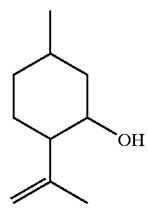

(1)

which comprises selectively cyclizing citronellal represented by the following formula (2):

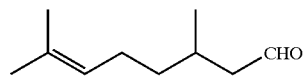

(2)

in the presence of a tris(2,6-diarylphenoxy)aluminum catalyst represented by the following formula (3):

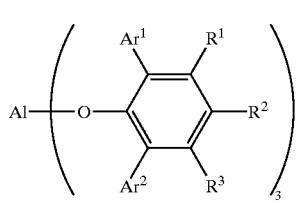

(3)

wherein Al represents an aluminum atom, $Ar^1$ and $Ar^2$ each represent a substituted or unsubstituted aryl group or a heteroaryl group, and $R^1$, $R^2$ and $R^3$ each represent a hydrogen atom, a halogen atom, an alkyl group having 1 to 8 carbon atom(s), an alkoxy group having 1 to 8 carbon atom(s), a substituted or unsubstituted aryl group, a dialkylamino group wherein each alkyl group has 1 to 4 carbon atom(s), or a nitro group.

2) A process for producing optically active isopulegol represented by the following formula (4):

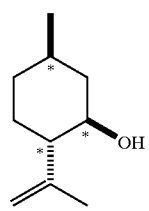

(4)

wherein * indicates an asymmetric carbon atom, which comprises selectively cyclizing optically active citronellal represented by the following formula (5):

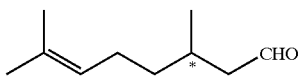
(5)

wherein * indicates an asymmetric carbon atom, in the presence of a tris(2,6-diarylphenoxy)aluminum catalyst represented by the following general formula (3):

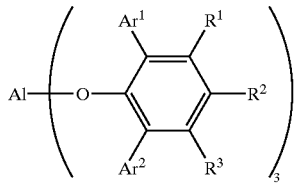
(3)

wherein Al, $Ar^1$, $Ar^2$, $R^1$, $R^2$, and $R^3$ are as defined above.

3) The process described in (1) or (2) above, wherein the tris(2,6-diarylphenoxy)aluminum catalyst is a reaction product obtained by reacting at least one aluminum compound selected from an alkylaluminum compound represented by the following general formula (6a):

$$(R^4)_{3-p}AlH_p \quad (6a)$$

wherein Al represents an aluminum atom, $R^4$ represents an alkyl group having 1 to 4 carbon atom(s), and p represents an integer of 0 to 2, and a metal aluminum hydride represented by the following general formula (6b):

$$MAlH_4 \quad (6b)$$

wherein M represents a lithium atom, a sodium atom or a potassium atom, and Al represents an aluminum atom; and a 2,6-diarylphenol represented by the following general formula (7):

(7)

wherein $Ar^1$, $Ar^2$, $R^1$, $R^2$, and $R^3$ are as defined above, in an inert solvent.

DETAILED DESCRIPTION OF THE INVENTION

The process for producing isopulegol according to the present invention is represented by the following reaction scheme:

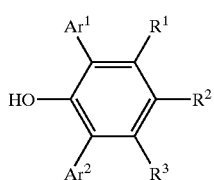
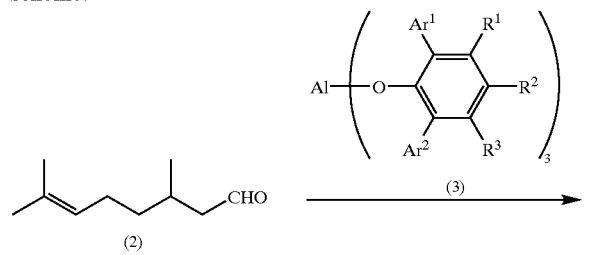
(3)

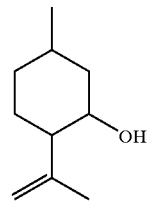
(1)

wherein Al, $Ar^1$, $Ar^2$, $R^1$, $R^2$, and $R^3$ are as defined above.

That is, citronellal (2) is selectively cyclized in the presence of a tris(2,6-diarylphenoxy)aluminum catalyst (3) to produce isopulegol (1).

Commercially available citronellal can be used as a starting compound (2) or (5).

In formula (6a) representing an alkylaluminum compound used to prepare the tris(2,6-diarylphenoxy)aluminum catalyst (3), $R^4$ represents an alkyl group having 1 to 4 carbon atom(s), and p presents an integer of 0 to 2.

$R^4$ includes methyl, ethyl, propyl, isopropyl, n-butyl, isobutyl, sec-butyl, and tert-butyl.

Examples of the alkylaluminum compound (6a) are trimethylaluminum, triethylaluminum, tripropylaluminum, tributylaluminum, dimethylaluminum hydride, diethylaluminum hydride, dipropylaluminum hydride, dibutylaluminum hydride, methylaluminum dihydride, ethylaluminum dihydride, propylaluminum dihydride, and butylaluminum dihydride.

In formula (6b) representing a metal aluminum hydride, M represents a lithium atom, a sodium atom or a potassium atom.

Examples of the metal aluminum hydride (6b) are lithium aluminum hydride, sodium aluminum hydride, and potassium aluminum hydride.

In formula (7) representing a 2,6-diarylphenol used to prepare the tris(2,6-diarylphenoxy)aluminum compound, $Ar^1$ and $Ar^2$ independently represent a substituted or unsubstituted aryl group or a heteroaryl group, $R^1$, $R^2$, and $R^3$ independently represent a hydrogen atom, a halogen atom, an alkyl group having 1 to 8 carbon atom(s), an alkoxy group having 1 to 8 carbon atom(s), a substituted or unsubstituted aryl group, a dialkylamino group wherein each alkyl group has 1 to 4 carbon atom(s) or a nitro group.

Examples of $Ar^1$ and $Ar^2$ include a phenyl group which may have from 1 to 5 substituent(s) such as an alkyl group having 1 to 4 carbon atom(s) (e.g., methyl, ethyl, propyl, isopropyl, n-butyl, isobutyl, sec-butyl or tert-butyl), an alkoxy group having 1 to 4 carbon atom(s) (e.g., methoxy, ethoxy, propoxy, isopropoxy, butoxy, isobutoxy, sec-butoxy or tert-butoxy), a halogen atom (e.g., fluorine, chlorine, bromine or iodine), etc.; a naphthyl group which may have from 1 to 7 substituent(s) such as an alkyl group having 1 to 4 carbon atom(s) (e.g., methyl, ethyl, propyl, isopropyl, n-butyl, isobutyl, sec-butyl or tert-butyl), an alkoxy group having 1 to 4 carbon atom(s) (e.g., methoxy, ethoxy, propoxy, isopropoxy, butoxy, isobutoxy, sec-butoxy or tert-butoxy), a halogen atom (e.g., fluorine, chlorine, bromine or iodine), etc.; and a heteroaryl group, such as furyl, thienyl, pyronyl, benzofuryl, isobenzofuryl, benzothienyl, indolyl, isoindolyl, carbazolyl, pyridyl, quinolyl, isoquinolyl, and pyrazyl groups.

Examples of $R^1$, $R^2$, and $R^3$ include a hydrogen atom; a halogen atom such as fluorine, chlorine, bromine or iodine; an alkyl group having 1 to 8 carbon atom(s) such as methyl, ethyl, propyl, isopropyl, n-butyl, isobutyl, sec-butyl, tert-butyl, pentyl, hexyl, heptyl, and octyl; an alkoxy group having 1 to 8 carbon atom(s) such as methoxy, ethoxy, propoxy, isopropoxy, butoxy, isobutyoxy, sec-butoxy, tert-butoxy, pentoxy, hexoxy, heptoxy, and octoxy; a phenyl group which may have from 1 to 5 substituent(s) such as an alkyl group having 1 to 4 carbon atom(s) (e.g., methyl, ethyl, propyl, isopropyl, n-butyl, isobutyl, sec-butyl or tert-butyl), an alkoxy group having 1 to 4 carbon atom(s) (e.g., methoxy, ethoxy, propoxy, isopropoxy, butoxy, isobutoxy, sec-butoxy or tert-butoxy), a halogen atom (e.g., fluorine, chlorine, bromine or iodine), etc.; a naphthyl group which may have from 1 to 7 substituent(s) such as an alkyl group having 1 to 4 carbon atom(s) (e.g., methyl, ethyl, propyl, isopropyl, n-butyl, isobutyl, sec-butyl or tert-butyl), an alkoxy group having 1 to 4 carbon atom(s) (e.g., methoxy, ethoxy, propoxy, isopropoxy, butoxy, isobutoxy, sec-butoxy or tert-butoxy), a halogen atom (e.g., fluorine, chlorine, bromine or iodine), etc.; a dialkylamino group wherein each alkyl group has 1 to 4 carbon atom(s), such as dimethylamino, diethylamino, dipropylamino, diisopropylamino, and dibutylamino; and a nitro group.

The tris(2,6-diarylphenoxy)aluminum catalyst (3) can easily be synthesized by the process described, e.g., in Yamamoto, H. et al., *J. Am. Chem. Soc.*, vol. 116, pp. 4131–4132 (1994).

As the process for preparing the tris(2,6-diarylphenoxy) aluminum catalyst (3), it can easily be prepared by, for example, allowing at least one aluminum compound selected from the alkylaluminum compound (6a) and the metal aluminum hydride (6b) to react with the 2,6-diarylphenol (7) of a molar quantity about 3 times as much as the aluminum compound (6) in an inert organic solvent, such as a hydrocarbon (e.g., hexane, heptane, benzene, toluene or xylene) or an ether (e.g., diethyl ether, diisopropyl ether or tetrahydrofuran) at a temperature of about 0 to 50° C. for about 30 minutes.

In the tris(2,6-diarylphenoxy)aluminum catalyst (3), $Ar^1$ and $Ar^2$ independently represent a substituted or unsubstituted aryl group or a heteroaryl group, and $R^1$, $R^2$ and $R^3$ independently represent a hydrogen atom, a halogen atom, an alkyl group having 1 to 8 carbon atom(s), an alkoxy group having 1 to 8 carbon atom(s), a dialkylamino group wherein each alkyl group has 1 to 4 carbon atom(s), or a nitro group. Examples of $Ar^1$, $Ar^2$, $R^1$, $R^2$ and $R^3$ are the same as those recited above.

The tris(2,6-diarylphenoxy)aluminum catalysts represented by formula (3) preferably include, but are not limited to, the compounds shown in Tables 1 to 3 below. Symbols used in the Tables 1 to 3 have the following meanings, which also apply to those used elsewhere in the present invention. The numerals used in combination with the symbols indicate the position of substitution on a phenyl group. For example, "4-Me—Ph" stands for a phenyl group substituted by a methyl group at the 4-position, and "3,4-F—Ph" stands for a phenyl group di-substituted by a fluorine atom at the 3-position and 4-position.

| H: | hydrogen |
|---|---|
| Ph: | phenyl group |
| Me: | methyl group |
| Xy: | xylyl group |
| iPr: | isopropyl group |
| tBu: | tert-butyl group |
| Np: | naphthyl group |
| F: | fluorine atom |
| Cl: | chlorine atom |
| MeO: | methoxy group |
| Furyl: | furyl group |
| ThioPh: | thiophenyl group |
| Py: | pyridinyl group |
| Cy: | cyclohexyl group |
| $Me_2N$: | dimethylamino group |
| benzene: | benzene ring fused to the benzene ring to form a naphthyl group |

TABLE 1

| Compound No. | $Ar^1$ | $Ar^2$ | $R^1$ | $R^2$ | $R^3$ |
|---|---|---|---|---|---|
| 1 | Ph | Ph | H | H | H |
| 2 | 4-Me—Ph | 4-Me—Ph | H | H | H |
| 3 | 3-Me—Ph | 3-Me—Ph | H | H | H |
| 4 | 2-Me—Ph | 2-Me—Ph | H | H | H |
| 5 | 2,4-Xy | 2,4-Xy | H | H | H |
| 6 | 2-iPr—Ph | 2-iPr—Ph | H | H | H |
| 7 | 4-tBu-Ph | 4-tBu-Ph | H | H | H |
| 8 | 4-Ph—Ph | 4-Ph—Ph | H | H | H |
| 9 | 4-Np—Ph | 4-Np—Ph | H | H | H |
| 10 | 4-F—Ph | 4-F—Ph | H | H | H |
| 11 | 4-Cl—Ph | 4-Cl—Ph | H | H | H |
| 12 | 3,4-F—Ph | 3,4-F—Ph | H | H | H |
| 13 | 3,4,5-F—Ph | 3,4,5-F—Ph | H | H | H |
| 14 | 4-MeO—Ph | 4-MeO—Ph | H | H | H |
| 15 | α-Np | α-Np | H | H | H |
| 16 | β-Np | β-Np | H | H | H |
| 17 | Furyl | Furyl | H | H | H |
| 18 | 2-ThioPh | 2-ThioPh | H | H | H |
| 19 | 3-ThioPh | 3-ThioPh | H | H | H |
| 20 | 4-ThioPh | 4-ThioPh | H | H | H |

TABLE 2

| Compound No. | $Ar^1$ | $Ar^2$ | $R^1$ | $R^2$ | $R^3$ |
|---|---|---|---|---|---|
| 21 | 2-Py | 2-Py | H | H | H |
| 22 | 3-Py | 3-Py | H | H | H |
| 23 | 4-Py | 4-Py | H | H | H |
| 24 | Ph | Ph | H | Me | H |
| 25 | Ph | Ph | H | tBu | H |
| 26 | Ph | Ph | H | Ph | H |
| 27 | Ph | Ph | H | Np | H |
| 28 | Ph | Ph | H | F | H |
| 29 | Ph | Ph | H | Cl | H |
| 30 | Ph | Ph | H | MeO | H |
| 31 | Ph | Ph | H | $Me_2N$ | H |
| 32 | Ph | Ph | H | $NO_2$ | H |
| 33 | Ph | Ph | H | Cy | H |
| 34 | Ph | Ph | Me | H | Me |
| 35 | Ph | Ph | Ph | H | Ph |
| 36 | 2-Me—Ph | 2-Me—Ph | Me | H | Me |
| 37 | 2-iP—Ph | 2-iP—Ph | Me | H | Me |
| 38 | α-Np | α-Np | Me | H | Me |
| 39 | Ph | 4-Me—Ph | H | H | H |
| 40 | Ph | 4-Me—Ph | H | Me | H |

TABLE 3

| Compound No. | $Ar^1$ | $Ar^2$ | $R^1$ | $R^2$ | $R^3$ |
|---|---|---|---|---|---|
| 41 | Ph | Xy | H | H | H |
| 42 | Ph | Ph | H | Me | H |
| 43 | Ph | 4-Cl—Ph | H | H | H |
| 44 | Ph | 4-Cl—Ph | H | Me | H |
| 45 | Ph | α-Np | H | H | H |
| 46 | Ph | α-Np | H | Me | H |

TABLE 3-continued

| Compound No. | $Ar^1$ | $Ar^2$ | $R^1$ | $R^2$ | $R^3$ |
|---|---|---|---|---|---|
| 47 | Ph | α-Np | | benzene | H |
| 48 | 4-F—Ph | α-Np | | benzene | H |

Still preferred tris(2,6-diarylphenoxy)aluminum catalyst are tris(2,6-diphenylphenoxy)aluminum (compound No. 1), tris[2,6-di(4-fluorophenyl)phenoxy]aluminum (compound No. 10), tris[2,6-di(3,4-difluorophenyl)phenoxy]aluminum (compound No. 12), tris[2,6-di(3,4,5-trifluorophenyl)phenoxy]aluminum (compound No. 13), tris(2,6-diphenyl-4-methylphenoxy)aluminum (compound No. 25), tris(2,6-diphenyl-3,5-dimethylphenoxy)aluminum (compound No. 34), tris[2,6-di(2-methylphenyl)-3,5-dimethylphenoxy]aluminum (compound No. 36), tris[2,6-di(2-isopropylphenyl)-3,5-dimethylphenoxy]aluminum (compound No. 37), tris[2,6-di(α-naphthyl)-3,5-dimethylphenoxy]aluminum (compound No. 38), tris(3-phenyl-1,1'-binaphthyl-2-oxy)aluminum (compound No. 47), and tris[3-(4-fluorophenyl)-1,1'-binaphthyl-2-oxy]aluminum (compound No. 48).

The tris(2,6-diarylphenoxy)aluminum catalyst (3) is used in an amount of about 0.05 to 5 mol %, preferably about 0.1 to 1 mol %, based on citronellal (2) or (5).

The cyclization reaction can be carried out either by (a) mixing the aluminum compound (6) (one compound selected from the alkylaluminum compound (6a) and the metal aluminum hydride (6b)) and the 2,6-diarylphenol (7) in a reaction system to prepare the catalyst and adding citronellal to the reaction system or (b) separately preparing the catalyst by mixing the aluminum compound (6) and the 2,6-diarylphenol (7) and adding citronellal and the catalyst to a reaction system. Either mode of reaction produces the same results.

The reaction is performed at a temperature ranging from about −60° to 100° C., preferably about −30° to 50° C., still preferably about −15° to 20° C., at which the reaction system is kept for about 0.25 to 30 hours, preferably about 0.5 to 20 hours, to give isopulegol (1) or (4) in a smooth manner.

The reaction is conducted either with or without an inert solvent.

The solvent is not particular limited and any solvent is usable unless the reaction is hindered appreciably. Illustrative examples include organic solvents such as aliphatic hydrocarbons (e.g., hexane, heptane and octane); alicyclic hydrocarbons (e.g., cyclohexane and methylcyclohexane); aromatic hydrocarbons (e.g., benzene, toluene, and xylene); and ethers (e.g., diethyl ether, diisopropyl ether, dimethoxyethane, tetrahydrofuran, dioxane, and dioxolane). Preferred of these organic solvents are toluene and heptane. It is preferred to use a previously dehydrated solvent.

The volume of the solvent, if used, is from about 0 to 20 times, preferably 0.5 to 7 times, the weight of citronellal.

The cyclization is preferably carried out under an inert gas atmosphere, such as a nitrogen gas or argon gas atmosphere, for smooth progress of the reaction.

After completion of the reaction, the reaction mixture is worked-up in a conventional manner. The product isopulegol (1) or (4) can be purified by distillation and recrystallization to give high-purity isopulegol.

The present invention will now be illustrated in greater detail with reference to Examples and Comparative Examples, but it should be understood that the invention is not deemed to be limited thereto, and modifications can be added thereto within the scope of the invention.

The products obtained in Examples were analyzed by gas chromatography (GLC). The conditions are as follows.

Analyzer used: Gas chromatograph G5000 supplied by Hitachi, Ltd.

Column: TC-WAX (0.25 mm×30 mm) supplied by GL Science Inc.

Detector: a flame ionization detector (FID).

EXAMPLE 1

Synthesis of l-isopulegol

Into a 50 ml Schlenk tube were put 240 mg (1 mmol) of 2,6-diphenylphenol and 5 ml of toluene to prepare a solution at room temperature under an argon atmosphere. To the solution was added 0.35 ml of a 0.93 mol toluene solution of triethylaluminum ($Et_3Al$, 0.33 mmol), and the mixture was stirred at room temperature for 30 minutes to prepare a catalyst solution. The catalyst solution was cooled to 0° C., and 5.07 g (32.9 mmol) of d-citronellal (available from Takasago International Corp.) cooled to −15° C. was added thereto dropwise, followed by stirring at 0° C. for 4 hours. After completion of the reaction, 2 ml of a 8% sodium hydroxide aqueous solution was added to the reaction mixture, and 5.05 g of dodecane was added as an internal standard. The organic layer was analyzed by gas chromatography. As a result, the yield of l-isopulegol was 95.3% and the ratio of l-isopulegol to other isomers was 99.3/0.7.

EXAMPLES 2 TO 12

Reaction was carried out in the same manner as in Example 1, except for changing the kind or the amount of the aluminum compound, the amounts of phenols and the solvents as shown in Table 4 below. The results obtained are shown in Table 4.

EXAMPLE 13

Synthesis of l-isopulegol

Into a 100 ml reaction vessel were put 4.79 g of 2,6-diphenylphenol and 40 ml of toluene at room temperature under an argon atmosphere to prepare a solution. To the solution was added 7 ml of a toluene solution of triethylaluminum ($Et_3Al$, 0.93 mol), and the mixture was stirred at room temperature for 30 minutes to prepare a catalyst solution. Separately, 100 g of d-citronellal (available from Takasago International Corp.) and 55 ml of toluene were put into a 300 ml reaction vessel under an argon atmosphere, and the mixture was cooled to 0° C. The whole amount of the catalyst solution prepared above and cooled to 0° C. was added thereto dropwise, followed by stirring at 0 C. for 4 hours. After completion of the reaction, 50 ml of a 4% sodium hydroxide aqueous solution was added to the reaction mixture, followed by liquid-liquid separation. Toluene was removed by evaporation, and the residue was distilled. A fraction having a boiling point of 91° C./1200 Pa (9 mmHg) was collected as a colorless oily product weighing 87.7 g. As a result of analysis by gas chromatography, it was found that l-isopulegol had been produced with a purity of 94.7% in a yield of 83.1% at an l-isopulegol to other isomers ratio of 99.7/0.3.

EXAMPLE 14

Synthesis of d-isopulegol

Into a 30 ml reaction vessel were put 1.21 g of 2,6-diphenylphenol and 15 ml of toluene under an argon atmosphere at room temperature to prepare a solution. To the solution was added 1.75 ml of a toluene solution of triethylaluminum (Et₃Al, 0.93 mol), and the mixture was stirred at room temperature for 30 minutes to prepare a catalyst solution. Separately, 5 g of l-citronellal (available from Takasago International Corp.) was put into a 50 ml reaction vessel and cooled to −15° C. under an argon atmosphere. The whole amount of the above prepared catalyst solution cooled to −15° C. was added dropwise to the citronellal. The mixture was stirred at −15° C. for 1 hour, then at −10° C. for 1 hour, and finally at −5° C. for 2 hours. After completion of the reaction, 20 ml of a 2% sodium hydroxide aqueous solution was added to the reaction mixture, followed by After completion of the reaction, 2 ml of a 4% sodium hydroxide aqueous solution was added to the reaction mixture, and 1.14 g of dodecane was added as an internal standard. The organic layer was analyzed by gas chromatography. As a result, the yield of l-isopulegol was 95.0% and the ratio of l-isopulegol to other isomers was 99.6/0.4.

The amount of the catalyst, the amount of the solvent used, the reaction temperature, reaction time, yield of isopulegol and the ratio of isopulegol to other isomers in Examples 1 to 16 are shown in Table 4 below.

TABLE 4

| Example | Catalyst | | Solvent | Reaction Conditions | | Yield | Isopulegol/ |
| | $R_3Al$ (mol %) | 2,6-diphenyl-phenol (mol %) | (ml/g-citronellal) | Temp. (° C.) | Time (hr) | (%) | other Isomers Ratio |
|---|---|---|---|---|---|---|---|
| 1 | Et₃Al (1) | 3 | toluene (1) | 0 | 4 | 95.3 | 99.3/0.7 |
| 2 | Et₃Al (5) | 15 | toluene (7) | 50 | 1 | 82.5 | 99.3/0.7 |
| 3 | Et₃Al (5) | 15 | toluene (7) | 25 | 1 | 88.7 | 99.3/0.7 |
| 4 | Et₃Al (5) | 16.5 | toluene (7) | 25 | 1 | 88.1 | 99.3/0.7 |
| 5 | Et₃Al (5) | 15 | toluene (7) | 0 | 4 | 96.5 | 99.4/0.6 |
| 6 | Me₃Al (5) | 15 | toluene (7) | 0 | 4 | 88.8 | 99.5/0.5 |
| 7 | Et₃Al (1) | 3 | toluene (7) | 50 | 17 | 47.9 | 99.2/0.8 |
| 8 | Et₃Al (1) | 3 | toluene (7) | 25 | 17 | 62.6 | 99.4/0.6 |
| 9 | Et₃Al (1) | 3 | toluene (7) | 0 | 17 | 95.2 | 99.4/0.6 |
| 10 | Et₃Al (0.5) | 1.5 | toluene (1) | 0 | 15 | 89.7 | 99.6/0.4 |
| 11 | Et₃Al (0.25) | 0.75 | toluene (1) | 0 | 17 | 71.8 | 99.6/0.4 |
| 12 | Et₃Al (0.25) | 0.75 | none | 0 | 17 | 51.9 | 99.7/0.3 |
| 13 | Et₃Al (1) | 3 | toluene (1) | 0 | 4 | 83.1 | 99.7/0.3 |
| 14 | Et₃Al (1) | 3 | toluene (3) | −15 to −5 | 4 | 82.3 | 99.4/0.6 |
| 15 | Et₃Al (1) | 3 | toluene (1) | 0 | 4 | 95.1 | 99.4/0.6 |
| 16 | Et₃Al (5) | 15 | none | −15 to 5 | 17 | 95.0 | 99.6/0.4 | liquid-liquid separation. Toluene was removed by evaporation, and the residue was distilled to obtain a colorless oily product weighing 4.19 g. As a result of analysis by gas chromatography, it was found that d-isopulegol had been produced with a purity of 98.2% in a yield of 82.3% at a d-isopulegol to other isomers ratio of 99.4/0.6.

EXAMPLE 15

Synthesis of dl-isopulegol

In Example 15, isopulegol was synthesized in the same manner as in Example 1, except for replacing d-citronellal with 5.00 g of dl-citronellal. As a result, dl-isopulegol was obtained in a yield of 95.1%, and the ratio of dl-isopulegol to other isomers was 99.4/0.6.

EXAMPLE 16

(1) Into a 50 ml Schlenk tube were put 1.03 g of 2,6-diphenylphenol and 13.5 ml of toluene under an argon atmosphere at room temperature to prepare a solution. To the solution was added 1.5 ml of a toluene solution of triethylaluminum (Et₃Al, 0.93 mol), and the mixture was stirred at room temperature for 30 minutes to prepare a pale yellow catalyst solution. The solvent was removed from the catalyst solution by evaporation in a high vacuum to give 1.06 g of the catalyst as pale yellow powder.

(2) In a 50 ml Schlenk tube was charged 1.01 g of d-citronellal and cooled to −15° C. under an argon atmosphere. The catalyst powder (249 mg) obtained in (1) above was added thereto, and the temperature was elevated up to 5° C. while stirring over a period of 17 hours.

Comparative Example 1

Under an argon atmosphere, 55 mg of zinc bromide was added to a 50 ml Schlenk tube, and 28 ml of a 15% toluene solution of d-citronellal (d-citronellal content: 3.82 g) was added thereto, followed by stirring at 110° C. for 17 hours. After the reaction, 2 ml of a 8% sodium hydroxide aqueous solution was added, and 1.23 g of dodecane was added thereto as an internal standard. The organic layer was analyzed by gas chromatography. As a result, the yield of l-isopulegol was 74.5% and the ratio of l-isopulegol to other isomers was 86.4/13.6. Other than l-isopulegol and the isomers, 0.7% of unreacted d-citronellal was found, the resist being high-boiling substances.

Comparative Example 2

Into a 50 ml Schlenk tube was put 73 mg of zinc bromide under an argon atmosphere, and 1.03 g of d-citronellal and 7 ml of toluene were added thereto, followed by stirring at 25° C. for 1 hour. After completion of the reaction, 5 ml of a 8% sodium hydroxide aqueous solution was added, and 1.12 g of dodecane was added thereto as an internal standard. The organic layer was analyzed by gas chromatography. As a result, the yield of l-isopulegol was 16.7% and the ratio of l-isopulegol to other isomers was 92.9/7.1.

Other than l-isopulegol and the isomers, 78.2% of unreacted d-citronellal was found, the rest being high-boiling substances.

Comparative Example 3

Into a 50 ml Schlenk tube were put 91.5 mg (1 mmol) of phenol and 7 ml of toluene under an argon atmosphere to form a solution. To the solution was added 0.35 ml of a 0.93 mol toluene solution containing 0.33 mmol of triethylaluminum (Et₃Al), followed by stirring at room temperature for 30 minutes to prepare a catalyst solution. Then, 1.02 g (6.62 mmol) of d-citronellal was added thereto dropwise, followed by stirring at 25° C. for 17 hours. After completion of the reaction, 2 ml of a 8% sodium hydroxide aqueous solution was added, and 1.12 g of dodecane was added thereto as an internal standard. The organic layer was analyzed by gas chromatography. As a result, the yield of l-isopulegol was 11.8% and the ratio of l-isopulegol to other isomers was 83.9/16.1.

Other than l-isopulegol and the isomers, 76.3% of unreacted d-citronellal was found, the rest consisting of high-boiling substances.

Comparative Example 4

As Comparative Example 4, isopulegol was synthesized in the same manner as in Comparative Example 3, except for replacing phenol with 166 mg of 2-phenylphenol. As a result of gas chromatography analysis, the yield of l-isopulegol was 19.3%, and the ratio of l-isopulegol to other isomers was 90.9/9.1.

Other than l-isopulegol and the isomers, 3.0% of unreacted d-citronellal was found, the rest being high-boiling substances.

Comparative Example 5

As Comparative Example 5, isopulegol was synthesized in the same manner as in Comparative Example 3, except for replacing phenol with 119 mg of 2,6-dimethylphenol and changing the reaction time to 1 hour. As a result of gas chromatography analysis, the yield of l-isopulegol was 14.1% and the ratio of l-isopulegol to other isomers was 85.3/14.7.

Other than l-isopulegol and the isomers, 11.6% of unreacted d-citronellal was found, the rest being high-boiling substances.

Comparative Example 6

As Comparative Example 6, isopulegol was synthesized in the same manner as in Comparative Example 3, except for replacing phenol with 201 mg of 2,6-di-tert-butylphenol. As a result of gas chromatography analysis, the yield of l-isopulegol was 0%.

Other than l-isopulegol and the isomers, 14.5% of unreacted d-citronellal was found, the rest being high-boiling substances.

The kinds and amounts of the catalysts used, the reaction temperature, reaction time, and the reaction yield of isopulegol and the ratio of isopulegol to other isomers, in Comparative Examples 1 to 6 are shown in Table 5 below.

TABLE 5

| Comp. Ex. | Catalyst (mol %) | Ligand (mol %) | Temp. (° C.) | Time (hr) | Yield (%) | Isopulegol/other three isomers ratio |
|---|---|---|---|---|---|---|
| 1 | ZnBr₂ (1) | none | 110 | 17 | 74.5 | 86.4/13.6 |
| 2 | ZnBr₂ (5) | none | 25 | 1 | 16.7 | 92.9/7.1 |
| 3 | Et₃Al (5) | phenol (15) | 25 | 17 | 11.8 | 83.9/16.1 |
| 4 | Et₃Al (5) | 2-phenyl-phenol (15) | 25 | 17 | 19.3 | 90.9/9.1 |

TABLE 5-continued

| Comp. Ex. | Catalyst (mol %) | Ligand (mol %) | Temp. (° C.) | Time (hr) | Yield (%) | Isopulegol/other three isomers ratio |
|---|---|---|---|---|---|---|
| 5 | Et₃Al (5) | 2,6-dimethylphenol (15) | 25 | 1 | 14.1 | 85.3/14.7 |
| 6 | Et₃Al (5) | 2,6-di-t-butylphenol (15) | 25 | 1 | 0 | — |

As is apparent from Tables 4 and 5, cyclization using tris(2,6-diarylphenoxy)aluminum catalyst of the present invention (Examples 1–16) makes it possible to produce isopulegol in good yield by cyclization at a convenient temperature (−15 to 50° C.). Neither an extremely low temperature or a high temperature is required. Cyclization using zinc bromide (Comparative Examples 1 and 2) as a catalyst instead of tris(2,6-diarylphenoxy)aluminum catalyst of the present invention attained a yield of 74.5% and an isopulegol to other isomers ratio of 86.4/13.6 at a high temperature (110° C. in Comparative Example 1), but the yield obtained at 25° C. (Comparative Example 2) was as low as 16.7%. It is understood that the zinc bromide requires high temperature. On the other hand, when phenol (no substituent on the 2,6-positions, Comparative Example 3), 2-phenylphenol (with an aryl group on only one of the 2,6-positions, Comparative Example 4) or 2,6-dimethylphenol or 2,6-di-tert-butylphenol (with an alkyl group on the 2,6-positions, Comparative Examples 5 and 6) was used as a ligand of an organoaluminum compound catalyst, the highest yield of isopulegol attained was 19.3%.

Thus, use of the tris(2,6-diarylphenoxy)aluminum catalyst according to the present invention in cyclization is of high utility in establishing synthesis of isopulegol.

The present invention provides a process for producing isopulegol, an important synthesis precursor for l-menthol and a useful material of aromas, etc., by using a tris(2,6-diarylphenoxy)aluminum catalyst in high yield at high selectivity.

While the invention has been described in detail and with reference to specific embodiments thereof, it will be apparent to one skilled in the art that various changes and modifications can be made therein without departing from the spirit and scope thereof.

This application is based on Japanese patent application No. 2001-10527 filed Jan. 18, 2001, the entire contents thereof being hereby incorporated by reference.

What is claimed is:

1. A process for producing isopulegol represented by the following formula (1):

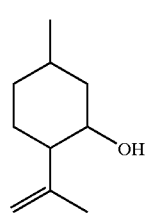

(1)

which comprises selectively cyclizing citronellal represented by the following formula (2):

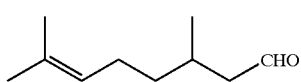
(2)

in the presence of a tris(2,6-diarylphenoxy)aluminum catalyst represented by the following general formula (3):

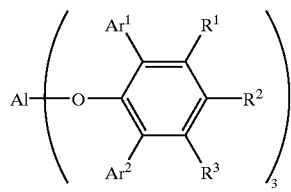
(3)

wherein Al represents an aluminum atom, $Ar^1$ and $Ar^2$ each represent a substituted or unsubstituted aryl group or a heteroaryl group; and $R^1$, $R^2$ and $R^3$ each represent a hydrogen atom, a halogen atom, an alkyl group having 1 to 8 carbon atom(s), an alkoxy group having 1 to 8 carbon atom(s), a substituted or unsubstituted aryl group, a dialkylamino group wherein each alkyl group has 1 to 4 carbon atom(s), or a nitro group.

2. A process for producing optically active isopulegol represented by the following formula (4):

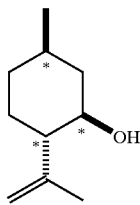
(4)

wherein * indicates an asymmetric carbon atom, which comprises selectively cyclizing optically active citronellal represented by the following formula (5):

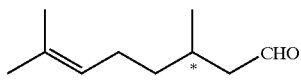
(5)

wherein * indicates an asymmetric carbon atom, in the presence of a tris(2,6-diarylphenoxy)aluminum catalyst represented by the following general formula (3):

(3)

wherein Al, $Ar^1$, $Ar^2$, $R^1$, $R^2$ and $R^3$ are as defined above.

3. A process for producing isopulegol according to claim 1 or 2, wherein said tris(2,6-diarylphenoxy)aluminum catalyst is a reaction product obtained by reacting at least one compound selected from an alkylaluminum compound represented by the following general formula (6a):

$$(R^4)_{3-p}AlH_p \qquad (6a)$$

wherein Al represents an aluminum atom, $R^4$ represents an alkyl group having 1 to 4 carbon atom(s), and p represents an integer of 0 to 2, and a metal aluminum hydride represented by the general formula (6b):

$$MAlH_4 \qquad (6b)$$

wherein M represents a lithium atom, a sodium atom or a potassium atom, and Al represents an aluminum atom; and a 2,6-diarylphenol represented by the following general formula (7):

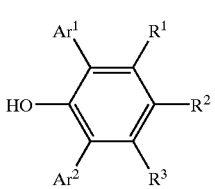
(7)

wherein $Ar^1$, $Ar^2$, $R^1$, $R^2$, and $R^3$ are as defined above, in an inert solvent.

* * * * *